US009625388B2

(12) United States Patent
Ishisaka et al.

(10) Patent No.: US 9,625,388 B2
(45) Date of Patent: Apr. 18, 2017

(54) CELL ANALYSIS APPARATUS AND CELL ANALYSIS METHOD

(75) Inventors: Masaki Ishisaka, Himeji (JP); Kazuki Kishi, Tokyo (JP); Masakazu Fukuda, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 495 days.

(21) Appl. No.: 12/762,703

(22) Filed: Apr. 19, 2010

(65) Prior Publication Data
US 2010/0196917 A1 Aug. 5, 2010

Related U.S. Application Data

(63) Continuation of application No. PCT/JP2008/069338, filed on Oct. 24, 2008.

(30) Foreign Application Priority Data

Oct. 29, 2007 (JP) ................. 2007-280738

(51) Int. Cl.
*G01N 21/64* (2006.01)
*G01N 15/14* (2006.01)
*G01N 15/00* (2006.01)

(52) U.S. Cl.
CPC ....... *G01N 21/6486* (2013.01); *G01N 15/147* (2013.01); *G01N 2015/0092* (2013.01); *G01N 2015/1497* (2013.01)

(58) Field of Classification Search
CPC ............ C12Q 1/6886; C12Q 2600/112; C12Q 2600/154; G01N 15/1434; G01N 15/1456;
(Continued)

(56) References Cited

U.S. PATENT DOCUMENTS 3,826,899 A * 7/1974 Ehrlich et al. .................. 377/10
4,660,971 A * 4/1987 Sage .................. G01N 15/1434
356/39

(Continued)

FOREIGN PATENT DOCUMENTS

EP 1 865 303 12/2007
EP 1865303 A1 * 12/2007 ............. G01N 15/14
(Continued)

OTHER PUBLICATIONS

International Search Report for International Application No. PCT/JP2008/069338, dated Feb. 3, 2009, 2 pages.

*Primary Examiner* — Robert T Crow
(74) *Attorney, Agent, or Firm* — Brinks Gilson & Lione

(57) ABSTRACT

A cell analysis apparatus that can accurately distinguish between an aggregating cell and a non-aggregating cell is provided. The cell analysis apparatus (10) includes: an optical detection section (3) for flowing a measurement sample obtained from a biological sample and a pigment into a flow cell (51), irradiating the measurement sample flowing in the flow cell (51) with laser beam and detecting fluorescence from the measurement sample; a signal processing circuit (4) for acquiring, based on a fluorescence signal outputted from the detection section (3), a value reflecting the height of a waveform of the signal and a value reflecting the length of a ridge line of the waveform of the signal; and a system control section (13) for distinguishing between an aggregating cell formed by aggregation of a plurality of cells and a non-aggregating cell, based on the value reflecting the height of the waveform of the fluorescence signal and the value reflecting the length of the ridge line of the waveform of the fluorescence signal obtained by the signal processing circuit (4).

8 Claims, 18 Drawing Sheets

(58) Field of Classification Search
CPC ......... G01N 15/147; G01N 2015/0092; G01N 2015/0244; G01N 2015/0294; G01N 2015/1488; G01N 2015/1497; G01N 2021/4707; G01N 2021/6486; G01N 2201/0612; G01N 33/49; G01N 33/493; G01N 33/57411

See application file for complete search history.

(56) References Cited

U.S. PATENT DOCUMENTS

| | | | |
|---|---|---|---|
| 5,109,429 A | | 4/1992 | Bacus et al. |
| 5,275,787 A | * | 1/1994 | Yuguchi ................ B01L 3/0268 209/579 |
| 5,488,469 A | * | 1/1996 | Yamamoto ......... G01N 15/1404 356/39 |
| 5,633,503 A | | 5/1997 | Kosaka |
| 2002/0071121 A1 | * | 6/2002 | Ortyn ..................... C07K 1/047 356/419 |
| 2002/0141902 A1 | * | 10/2002 | Ozasa et al. ............... 422/82.09 |
| 2004/0018629 A1 | | 1/2004 | Kawate |
| 2005/0221399 A1 | | 10/2005 | Nakano et al. |
| 2006/0211009 A1 | * | 9/2006 | An et al. .......................... 435/6 |
| 2007/0109530 A1 | * | 5/2007 | Ueno .................. G01N 15/1404 356/39 |
| 2008/0108103 A1 | | 5/2008 | Ishisaka et al. |

FOREIGN PATENT DOCUMENTS

| | | |
|---|---|---|
| JP | S58-032145 | 2/1983 |
| JP | S59-081539 | 5/1984 |
| JP | 04-006465 A | 1/1992 |
| JP | 06-019349 B | 3/1994 |
| JP | H07-151671 | 6/1995 |
| JP | 2002-188993 A | 7/2002 |
| JP | 2002-277381 | 9/2002 |
| JP | 2004-125775 A | 4/2004 |
| JP | 2005-315862 | 11/2005 |
| JP | 2006-524054 | 10/2006 |
| JP | 2006-330001 | 12/2006 |
| KP | H01-127956 | 5/1989 |
| WO | WO 2004/088283 | 10/2004 |
| WO | WO 2006/103920 | 10/2006 |
| WO | WO 2006/103920 A1 * 10/2006 ............ G01N 21/64 |

* cited by examiner (a)

(b)

(a)

(b)

——— Forward-scattered light
············ Lateral-scattered light
—·—·— Fluorescence (a)

(b)

CELL ANALYSIS APPARATUS AND CELL ANALYSIS METHOD

RELATED APPLICATIONS

This application is a continuation of PCT/JP2008/069338 filed on Oct. 24, 2008, which claims priority to Japanese Application No. JP2007-280738 filed on Oct. 29, 2007. The entire contents of these applications are incorporated herein by reference.

TECHNICAL FIELD

The present invention relates to a cell analysis apparatus and a cell analysis method. More particularly, the present invention relates to a cell analysis apparatus and a cell analysis method by which a measurement sample flowing in a flow cell is illuminated with laser beam and the light from the measurement sample is used to analyze cells in the measurement sample.

BACKGROUND ART

Flow cytometry method for illuminating a measurement sample including cells as a measuring object with laser beam and measuring the size and shape of each cell by using scattered light and fluorescence from the measurement sample, is disclosed in WO publication No. 2006/103920 for example. According to this flow cytometry method, a measurement sample including cells as a measuring object is surrounded by sheath liquid and is squeezed in a sheath flow cell to arrange the cells in one straight line to pass the flow cell. In this manner, a plurality of cells are suppressed from simultaneously passing through a detection region in the sheath flow cell.

However, cells may aggregate in the measurement sample. The existence of aggregating cells (a plurality of cells that aggregate) makes it difficult to accurately measure the sizes and shapes of the respective cells in the measurement sample for example.

In view of the above, according to an analysis apparatus disclosed in WO publication No. 2006/103920, forward-scattered light from a measurement sample illuminated with laser beam is detected. Then, a ratio between the difference integration value of the signal waveform of the obtained forward-scattered light and the peak value of the signal waveform is used to determine whether the signal waveform includes a trough or not to thereby distinguish between aggregating cells and non-aggregating cells (a plurality of cells that do not aggregate and each of which exists as a single cell).

SUMMARY OF THE INVENTION

However, the signal waveform of the forward-scattered light detected from cells has a height that changes depending on how the cells aggregate and a direction to which the cells flow for example. This consequently may cause a signal waveform of forward-scattered light that has unclear peak and trough. Thus, the analysis apparatus disclosed in WO publication No. 2006/103920 is limited in the improvement of the accuracy of distinguishing between aggregating cells and non-aggregating cells.

The present invention has been made in view of the situation as described above. It is an objective of the present invention to provide a cell analysis apparatus and a cell analysis method which is capable of distinguishing between aggregating cells and non-aggregating cells accurately.

The cell analysis apparatus according to a first aspect of this invention is a cell analysis apparatus for analyzing measuring object cells included in a biological sample, comprising: a detection section for flowing a measurement sample obtained from the biological sample and a pigment into a flow cell, irradiating the measurement sample flowing in the flow cell with laser beam, and detecting fluorescence from the measurement sample; a signal processing section for obtaining, based on a fluorescence signal outputted from the detection section, a value reflecting height of a waveform of the fluorescence signal and a value reflecting length of a ridge line of the waveform of the fluorescence signal; and an analysis section for distinguishing between an aggregating cell formed by aggregation of a plurality of cells and a non-aggregating cell, based on the value reflecting the height of the waveform of the fluorescence signal and the value reflecting the length of the ridge line of the waveform of the fluorescence signal obtained by the signal processing section.

The cell analysis apparatus according to a second aspect of this invention is a cell analysis apparatus for analyzing measuring object cells included in a biological sample, comprising: a detection section for flowing a measurement sample obtained from the biological sample and a pigment into a flow cell, irradiating the measurement sample flowing in the flow cell with laser beam, and detecting fluorescence from the measurement sample; a signal processing section for obtaining, based on a fluorescence signal outputted from the detection section, a first value reflecting height of a waveform of the fluorescence signal, a second value reflecting length of a ridge line of the waveform of the fluorescence signal, and a third value reflecting DNA amount of a nucleus of the measuring object cell; and an analysis section for classifying an abnormal cell from the measuring object cells included in the measurement sample, based on the first value, the second value, and the third value obtained by the signal processing section.

The cell analysis method according to a third aspect of this invention is a cell analysis method, comprising: a first step of preparing a measurement sample by mixing a biological sample with a pigment; a second step of flowing the prepared measurement sample into a flow cell, irradiating the measurement sample flowing in the flow cell with laser beam, and detecting fluorescence from the measurement sample; a third step of obtaining, based on a fluorescence signal generated from the fluorescence, a value reflecting height of a waveform of the fluorescence signal and a value reflecting length of a ridge line of the waveform of the fluorescence signal; and a fourth step of distinguishing between an aggregating cell formed by aggregation of a plurality of cells and a non-aggregating cell, based on the value reflecting the height of the waveform of the fluorescence signal and the value reflecting the length of the ridge line of the waveform of the fluorescence signal.

The cell analysis method according to a fourth aspect of this invention is a cell analysis method, comprising: a first step of preparing a measurement sample by mixing a biological sample with a pigment; a second step of flowing the prepared measurement sample into a flow cell, irradiating the measurement sample flowing in the flow cell with laser beam, and detecting fluorescence from the measurement sample; a third step of obtaining, based on a fluorescence signal generated from the fluorescence, a first value reflecting height of a waveform of the fluorescence signal, a second value reflecting length of a ridge line of the waveform of the fluorescence signal, and a third value reflecting DNA amount of a nucleus of the measuring object cell; and a fourth step of classifying an abnormal cell from the measuring object cells included in the measurement sample, based on the first value, the second value, and the third value.

DETAILED DESCRIPTION OF THE PREFERRED EMBODIMENTS

The following section will describe in detail an embodiment of a cell analysis apparatus and a cell analysis method of the present invention with reference to the attached drawings.

Entire Configuration of Cell Analysis Apparatus

Figure 1:
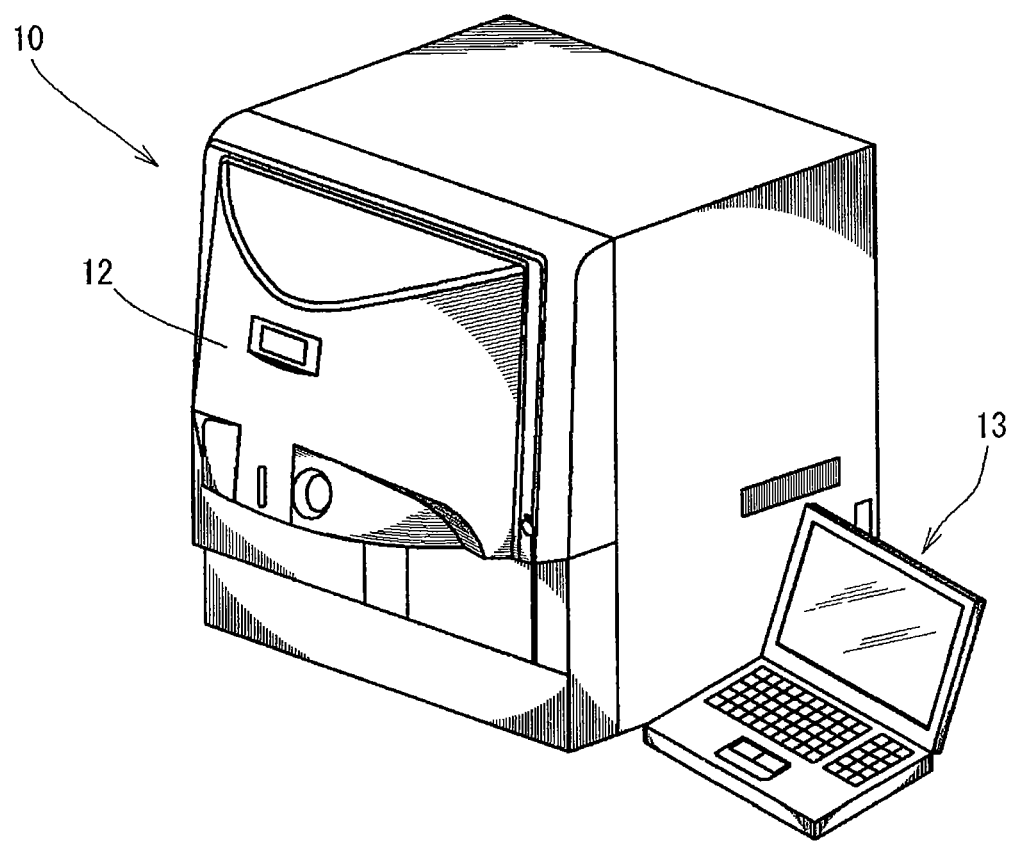
FIG. 1 is a perspective view illustrating one embodiment of a cell analysis apparatus of the present invention.

FIG. 1 is a perspective view illustrating a cell analysis apparatus 10 according to one embodiment of the present invention. The cell analysis apparatus 10 is used for the following process. Specifically, a measurement sample including cells collected from a patient is caused to flow into a flow cell. Then, the measurement sample flowing in the flow cell is irradiated with laser beam. Then, the light from the measurement sample (e.g., forward-scattered light or lateral fluorescence) is detected and analyzed to thereby determine whether the cells include cancer and atypical cells or not. Specifically, the cell analysis apparatus 10 is used for screening a cervical cancer by using epithelial cells of the endocervix. The cell analysis apparatus 10 includes: an apparatus main body 12 that measures a sample for example; and a system control section 13 that is connected to the apparatus main body 12 and that analyzes the measurement result for example.

Figure 2:
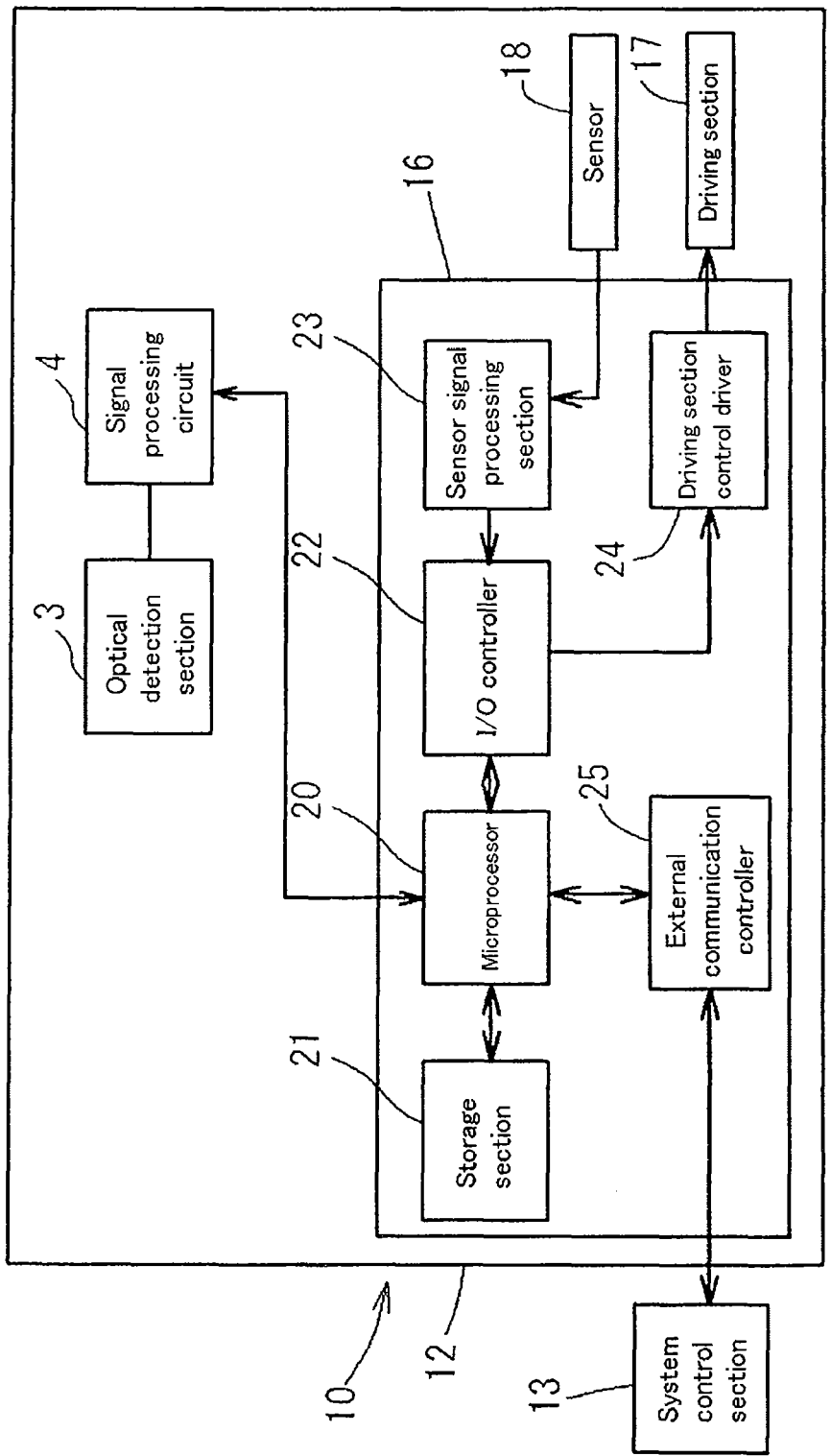
FIG. 2 is a block diagram illustrating the configuration of the cell analysis apparatus shown in FIG. 1.

As shown in FIG. 2, the apparatus main body 12 of the cell analysis apparatus 10 includes: an optical detection section 3 for detecting from the measurement sample the information such as cell or nucleus size information; a signal processing circuit 4; a measurement control section 16; a driving section 17 such as a motor, an actuator, and a valve; and various sensors 18. The signal processing circuit 4 includes: an analog signal processing circuit that subjects the result obtained by amplifying the output from the optical detection section 3 by a preamplifier (not shown) to an amplification processing or a filter processing or the like; an A/D converter that converts the output from the analog signal processing circuit to a digital signal; and a digital signal processing circuit that subjects the digital signal to a predetermined waveform processing. The measurement control section 16 controls the operation of the driving section 17 while processing the signal from the sensor 18 to thereby providing the suction and measurement of the measurement sample. The screening of a cervical cancer can be performed by preparing a measurement sample obtained by subjecting cells collected from the endocervix of the patient (epithelial cells) to known processings such as centrifugation (concentration), dilution (cleaning), agitation (tapping), or PI staining. The prepared measurement sample is stored in a test tube and the test tube is placed under a pipette (not shown) of the apparatus main body 12. Then, the sample is sucked by the pipette and is supplied to a flow cell. The PI staining is performed by propidium iodide (PI) that is fluorescence staining liquid including pigments. The PI staining can selectively stain a nucleus, thus allowing the detection of the fluorescence from the nucleus.

Configuration of Measurement Control Section

The measurement control section 16 includes, for example, a microprocessor 20, a storage section 21, an I/O controller 22, a sensor signal processing section 23, a driving section control driver 24, and an external communication controller 25. The storage section 21 is composed of ROM, RAM or the like. The ROM stores therein a control program for controlling the driving section 17 and the data required to execute the control program. The microprocessor 20 can load the control program to the RAM or can directly execute the control program from the ROM.

The microprocessor 20 receives the signal from the sensor 18 via the sensor signal processing section 23 and the I/O controller 22. The microprocessor 20 can execute the control program to thereby control, in accordance with the signal from the sensor 18, the driving section 17 via the I/O controller 22 and the driving section control driver 24.

The data processed by the microprocessor 20 and the data required for the processing by the microprocessor 20 are exchanged via the external communication controller 25 with an external apparatus such as the system control section 13.

Configuration of System Control Section

Figure 3:
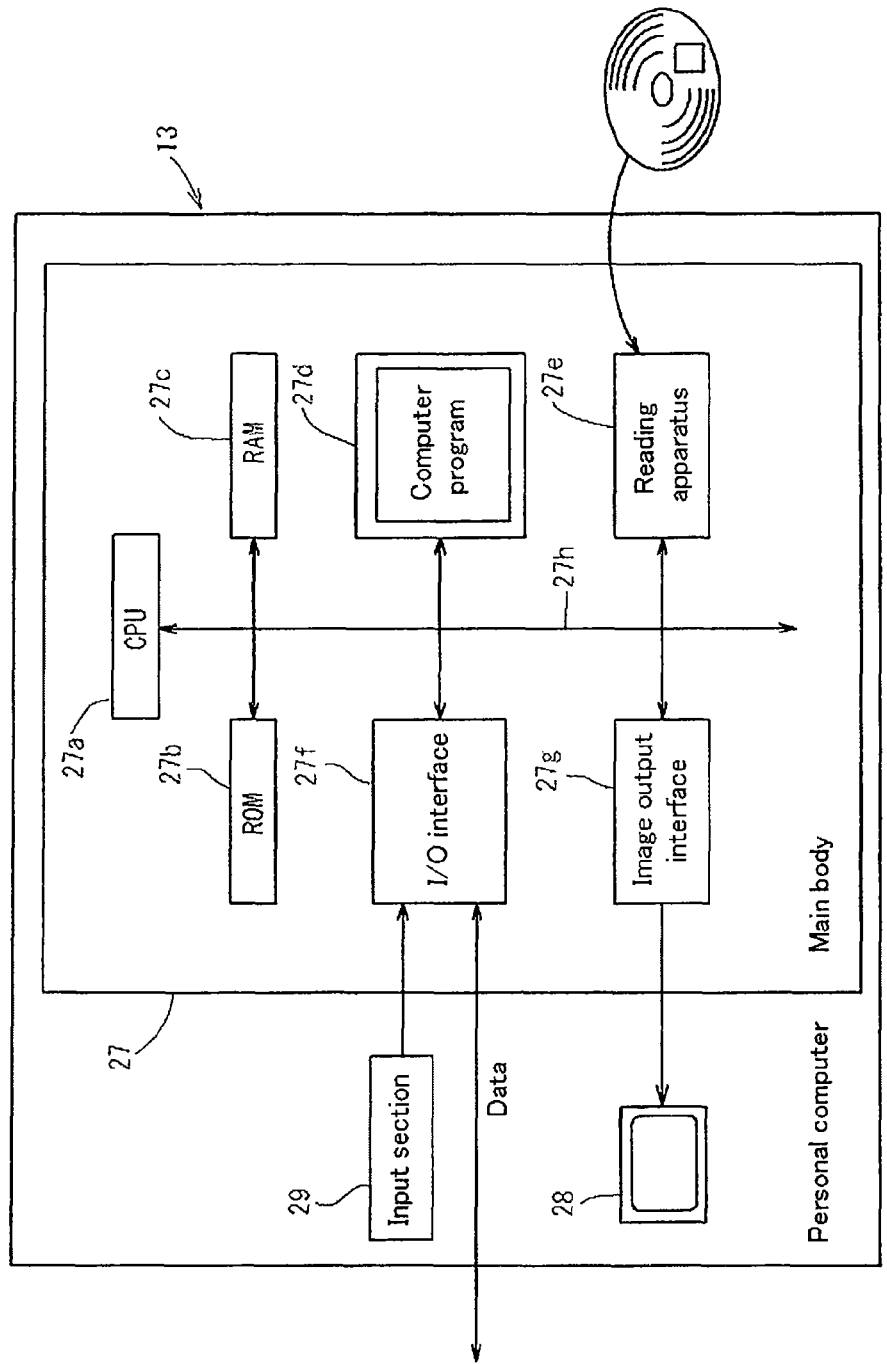
FIG. 3 is a block diagram illustrating a personal computer configuring a system control section.

FIG. 3 is a block diagram illustrating the system control section 13. The system control section 13 is composed of a personal computer for example and is mainly composed of a main body 27, a display section 28, and an input section 29. The main body 27 is mainly composed of a CPU 27a, a ROM 27b, a RAM 27c, a hard disk 27d, a reading apparatus 27e, an input/output interface 27f, and an image output interface 27g that are connected by a bus 27h so that communication can be provided thereamong.

The CPU 27a can execute a computer program stored in the ROM 27b and a computer program loaded to the RAM 27c. The ROM 27b is configured by a mask ROM, PROM, EPROM, or EEPROM for example. The ROM 27b stores therein a computer program executed by the CPU 27a and the data used for the computer program. The RAM 27c is configured by a SRAM or DRAM or the like. The RAM 27c is used to read computer programs recorded in the ROM 27b and the hard disk 27d and is also used as a work area of the CPU 27a for executing these computer programs.

In the hard disk 27d, there are installed various computer programs to be executed by the CPU 27a such as an operating system and an application program, and data used to execute the computer programs. For example, in the hard disk 27d, there is installed an operating system providing a graphical user interface environment such as Windows® manufactured and sold by US Microsoft Corporation. In the hard disk 27d, there are installed a computer program for determining aggregating particles and non-aggregating particles and the data used to execute the computer program.

In the hard disk 27d, there is also installed operation programs for sending a measurement order (operation instruction) to the measurement control section 16 of the cell analysis apparatus 10, receiving and processing the measurement result of the measurement by the apparatus main body 12, and displaying the processed analysis result for example. This operation program operates on the operating system.

The reading apparatus 27e is configured by a flexible disk drive, a CD-ROM drive, or a DVD-ROM drive for example and can read the computer program or data recorded in a portable recording medium. The input/output interface 27f is configured, for example, by a serial interface such as USB, IEEE 1394 or RS-232C, a parallel interface such as SCSI, IDE, or IEEE 1284, and an analog interface such as a D/A converter or A/D converter. The input/output interface 27f is connected with the input section 29 composed of a keyboard and a mouse. A user can use the input section 29 to input data to the personal computer. The input/output interface 27f is also connected to the apparatus main body 12 and can exchange data with the apparatus main body 12 for example.

The image output interface 27g is connected with the display section 28 composed of LCD or CRT for example. The image output interface 27g outputs to the display section 28 a video signal depending on the image data given from the CPU 27a. In accordance with the input video signal, the display section 28 displays an image (screen).

Configuration of Optical Detection Section

Figure 4:
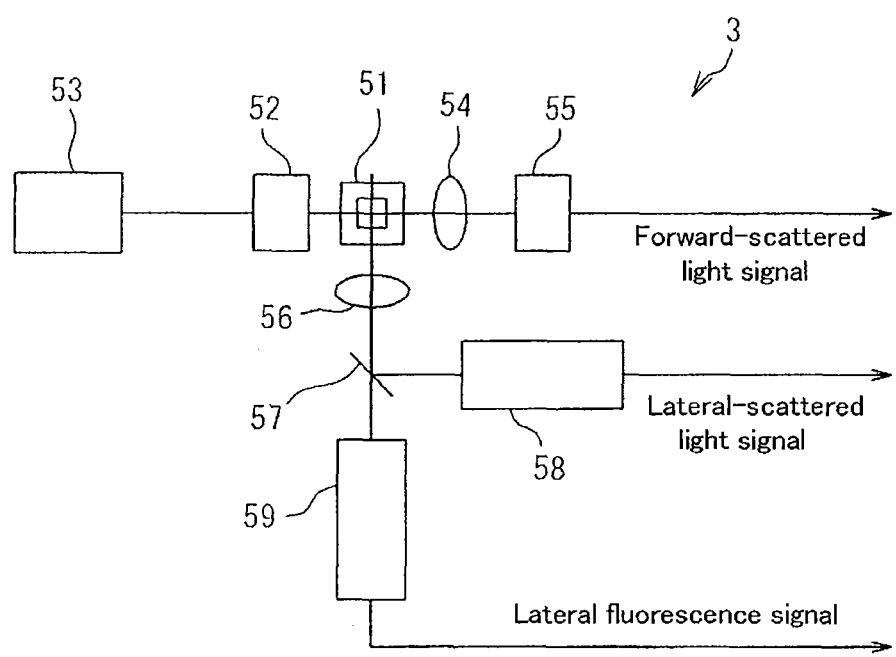
FIG. 4 illustrates the configuration of an optical detection section.

FIG. 4 illustrates the configuration of the optical detection section 3. In FIG. 4, a lens system (optical system) 52 collects the laser beam emitted from a semiconductor laser 53 as a light source to the measurement sample flowing in a flow cell 51. A light collection lens 54 causes the forward-scattered light from the cell in the measurement sample to be collected in a photodiode 55 as a scattered light detector. Although the lens system 52 is shown as a single lens for simplicity, the lens system 52 can be configured more specifically as shown in FIG. 13 and FIG. 14 as a lens group composed of, in an order from the semiconductor laser 53, a collimator lens 52a, a cylinder lens system (a plane-convex cylinder lens 52b+a biconcave cylinder lens 52c), and a condenser lens system (a condenser lens 52d+a condenser lens 52e).

Figure 13:
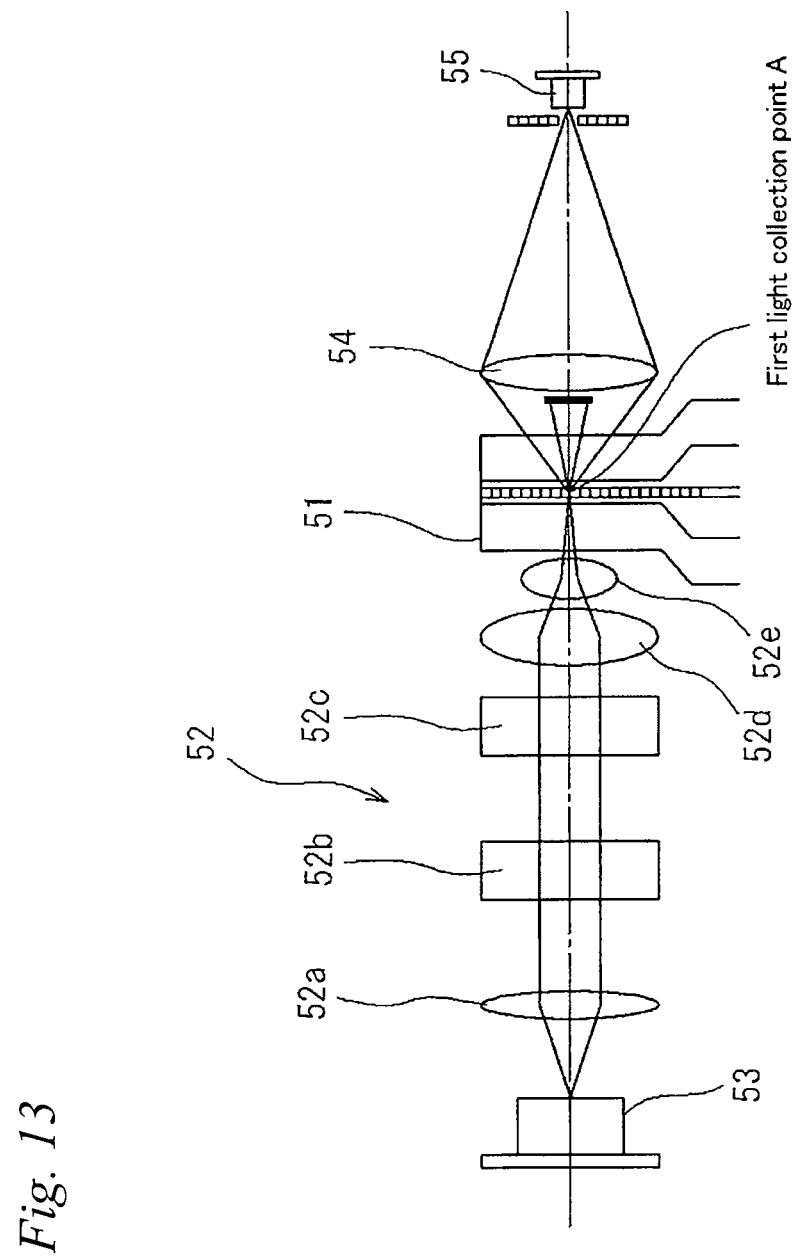
FIG. 13 is a side view illustrating an optical detection section.

As shown in FIG. 13, when the optical detection section 3 is seen from a side face, the radial laser beam emitted from the semiconductor laser 53 is converted by a collimator lens 52a to parallel light. The parallel light passes the plane-convex cylinder lens 52b and the biconcave cylinder lens 52c without being bent. Then, the light is caused by the condenser lens 52d and the condenser lens 52e to be collected at the first light collection point A in the measurement sample flowing in the flow cell 51.

Figure 14:
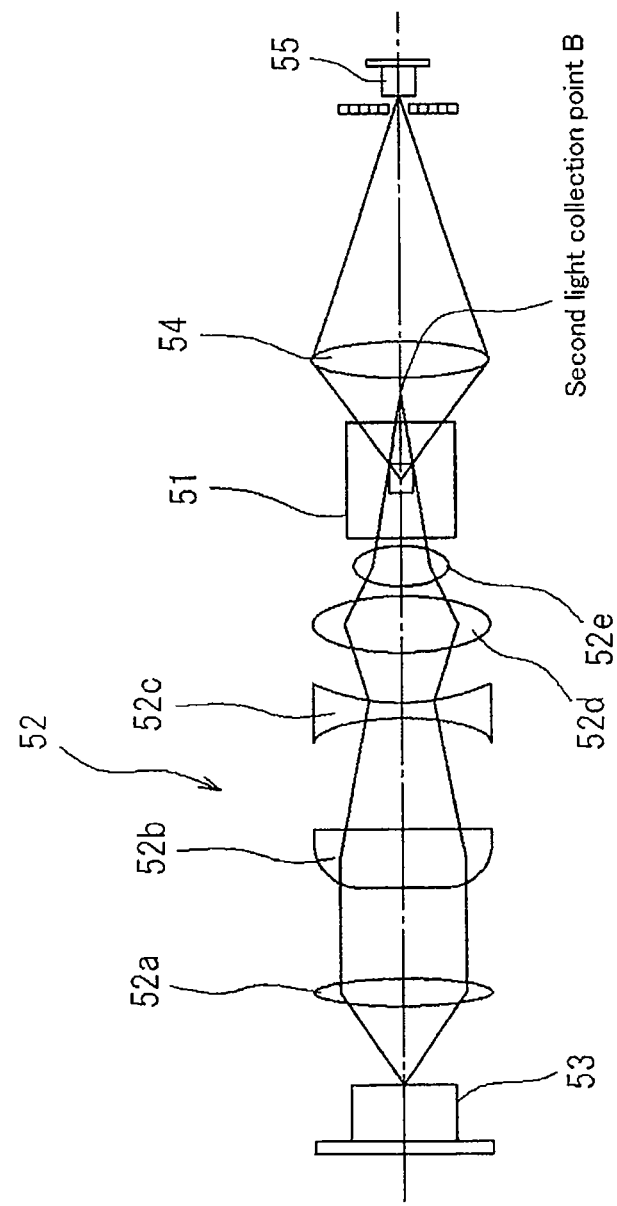
FIG. 14 is a top view illustrating the optical detection section.

When the optical detection section 3 is seen from the upper side as shown in FIG. 14 on the other hand, the radial laser beam emitted from the semiconductor laser 53 is converted by the collimator lens 52a to parallel light. Then, the parallel light is caused by the plane-convex cylinder lens 52b to converge in a direction orthogonal to the direction to which the measurement sample flows. Then, the light is caused by the biconcave cylinder lens 52c to diverge in a direction orthogonal to the direction to which the measurement sample flows. Then, the light is collected by the condenser lens 52d and the condenser lens 52e at the second light collection point B at the rear side of the flow cell 51.

By the lens system 52 as described above, the beam shape at the first light collection point A (the beam shape seen from the semiconductor laser 53-side) is caused to converge in the direction to which the measurement sample flows. Then, the beam shape is a long ellipse-like shape extending in the direction orthogonal to the direction to which the measurement sample flows. Specifically, the beam spot having a diameter of 3 to 8 μm in the direction to which the measurement sample flows in the flow cell 51 and having a diameter of 300 to 600 μm in the direction orthogonal to the direction to which the measurement sample flows is emitted to the measurement sample flowing in the flow cell 51 while forming the first light collection point A on a plane passing the direction to which the measurement sample flows.

The lens system 52 is not limited to the above configuration and also may be changed appropriately.

Another light collection lens 56 collects the lateral-scattered light and the lateral fluorescence from the cell or the nucleus in the cell at a dichroic mirror 57. The dichroic mirror 57 reflects the lateral-scattered light to a photomultiplier 58 as a scattered light detector and transmits the lateral fluorescence to a photomultiplier 59 as a fluorescence detector. These lights reflect the features of the cell and nucleus in the measurement sample. Then, the photodiode 55, the photomultiplier 58, and the photomultiplier 59 convert the detected light to electric signals to output a forward-scattered light signal (FSC), a lateral-scattered light signal (SSC), and a lateral fluorescence signal (SFL), respectively. These signals are amplified by a preamplifier (not shown). Then, the signals are sent to the above-described signal processing circuit 4 (see FIG. 2).

As shown in FIG. 2, the forward-scattered light data (FSC), the lateral-scattered light data (SSC), and the lateral fluorescence data (SFL) obtained by being subjected by the signal processing circuit 4 to a signal processing such as filter processing and A/D conversion processing are sent by the microprocessor 20 to the above-described system control section 13 via the external communication controller 25. Based on the forward-scattered light data (FSC), the lateral-scattered light data (SSC), and the lateral fluorescence data (SFL), the system control section 13 prepares a scattergram and a histogram for analyzing the cell and the nucleus.

Although the light source may be gas laser instead of the semiconductor laser, semiconductor laser is preferably used from the viewpoints of low cost, small size, and low power consumption. The use of semiconductor laser can reduce the product cost and also can provide the apparatus with a smaller size and power saving. In the present embodiment, blue semiconductor laser having a short wavelength is used that is advantageous in narrowing beam. The blue semiconductor laser is also advantageous to a fluorescence excitation wavelength such as PI. Among semiconductor lasers, red semiconductor laser also may be used that is low-cost and long-life, and that is stably supplied from manufacturers.

Figure 5:
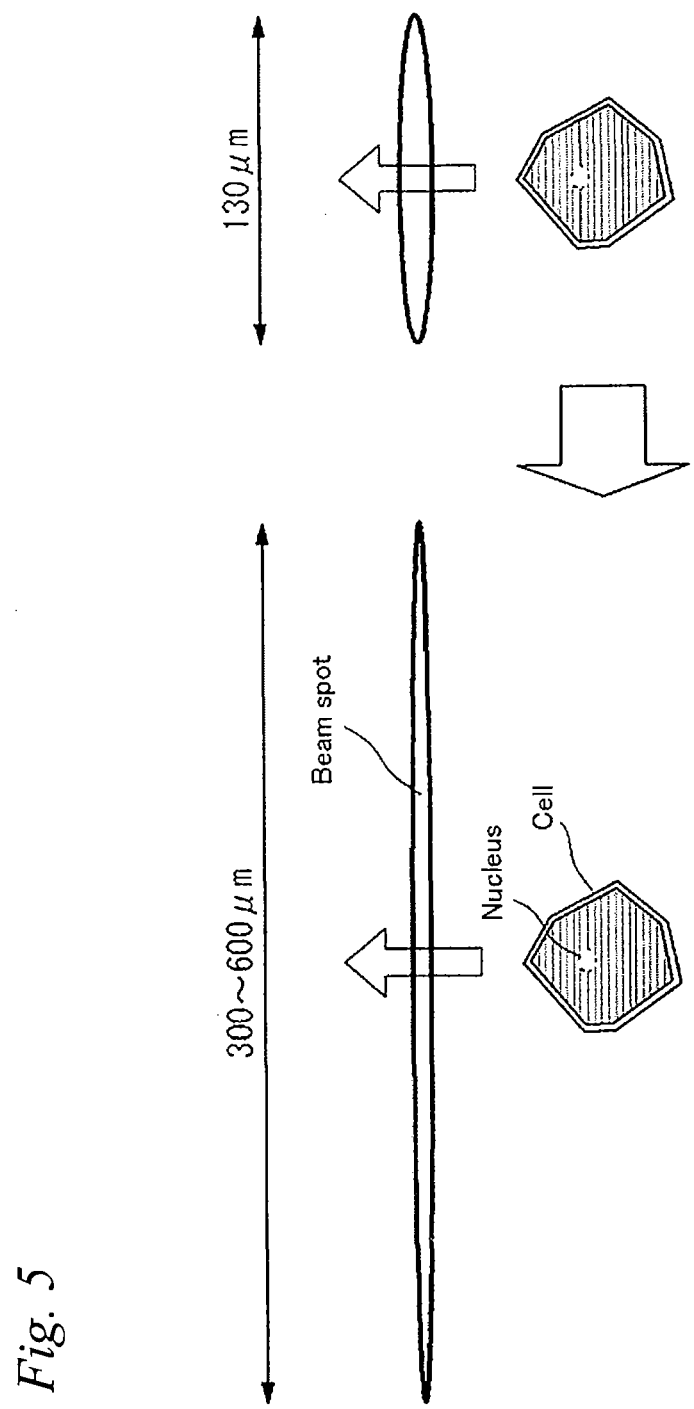
FIG. 5 illustrates a cell passing through a beam spot.

In the present embodiment, the lens system 52 (FIG. 4) as an optical system is used to form a beam spot having a predetermined size. Specifically, such a substantially-elliptical beam spot that has a diameter of 3 to 8 μm in the direction to which the measurement sample flows in the flow cell 51 and a diameter of 300 to 600 μm in the direction orthogonal to the direction to which the measurement sample flows is formed on the measurement sample. FIG. 5 illustrates the cell passing through the beam spot. In FIG. 5, the up-and-down direction is the direction to which the measurement sample flows in the flow cell. In FIG. 5, the right beam spot is a beam spot in a conventional general apparatus used to detect red blood cells and white blood cells in blood. The left beam spot is a beam spot formed by an optical system of a cell analysis apparatus according to the present embodiment. For the convenience of the drawing, the longitudinal size of the beam spot is reduced when compared to the size in the orthogonal direction (in the up-and-down direction). However, an actual beam spot of the present embodiment has a very long and thin cross-sectional shape.

Figure 9:
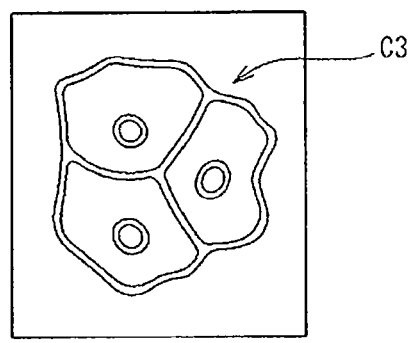
FIG. 9(a) shows aggregating cells C3 formed by aggregation of three cells.
FIG. 9(b) illustrates the signal waveform of an aggregating cell composed of three cells.
Figure 9:
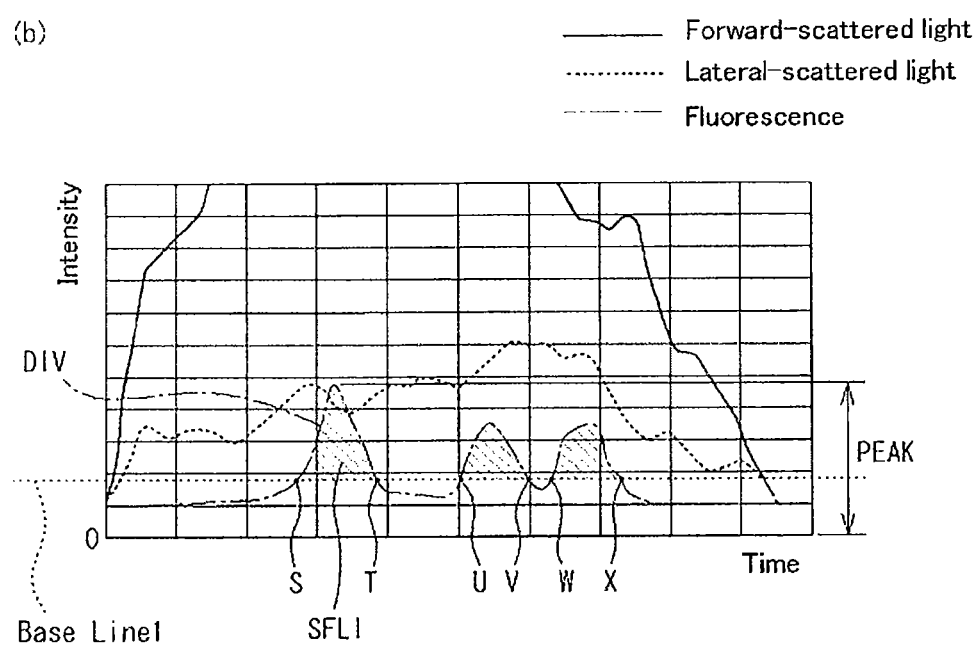

In the present embodiment, the fluorescence from the measurement sample flowing in the flow cell is detected by the photomultiplier 59. Based on the fluorescence signal output from the photomultiplier 59, the signal processing circuit 4 acquires a peak value (PEAK) of the fluorescence signal waveform as a value reflecting the height of the signal waveform. The signal processing circuit 4 also acquires a difference integration value (DIV) of the signal waveform as a value reflecting the length of the ridge line of the signal waveform. FIG. 9(*b*) illustrates the signal waveform of a cell C3 of FIG. 9(*a*) in which the vertical axis shows the detected light intensity and the horizontal axis shows the time at which an optical signal is detected. As shown in FIG. 9(*b*), the peak value (PEAK) of the fluorescence signal waveform (chain line) shows the maximum intensity of the detected fluorescence (PEAK in FIG. 9(*b*)) and the difference integration value (DIV) of the fluorescence signal waveform shows the length of the fluorescence signal waveform having a higher intensity than the base line (Base Line 1) (total of the lengths of the waveform from the point S to the point T, the waveform from the point U to the point V, and the waveform from the point W to the point X). The system control section 13 receives the lateral fluorescence data including the difference integration value (DIV) of the fluorescence signal waveform and the peak value (PEAK) of the fluorescence signal waveform via the external communication controller 25. Then, the system control section 13 compares a value (DIV/PEAK) obtained by dividing the difference integration value (DIV) of the fluorescence signal waveform by the peak value (PEAK) of the fluorescence signal waveform with a predetermined threshold value to thereby determine whether the cell is an aggregating cell or a non-aggregating cell.

A difference integration value is a value obtained by subjecting signal waveforms to differentiation to add up the resulting the absolute values. A difference integration value of a signal having no trough in the waveform is approximately equal to a value obtained by doubling the peak value of the signal. On the other hand, a difference integration value of a signal having a trough in the waveform is higher than a value obtained by doubling the peak value of the signal. An increase in the trough in the waveform and a deeper trough cause a larger difference from a value obtained by doubling the peak value.

In view of the above, the system control section 13 considers the noise superposed on the signal for example, and "2.6", which is a value slightly higher than "2", is used as the above "predetermined threshold value" functioning as a reference value for determining whether a measuring object cell is an aggregating cell or a non-aggregating cell. Although the predetermined threshold value is not limited to 2.6, the predetermined threshold value is preferably within a range from 2.2 to 3. When a value (DIV/PEAK) obtained by dividing the difference integration value (DIV) of the fluorescence signal waveform by the peak value (PEAK) of the fluorescence signal waveform is higher than the predetermined threshold value, it means that the fluorescence signal waveform includes at least one trough. Thus, the measuring object cell can be classified as an aggregating cell which is an aggregation of a plurality of cells.

Figure 6:
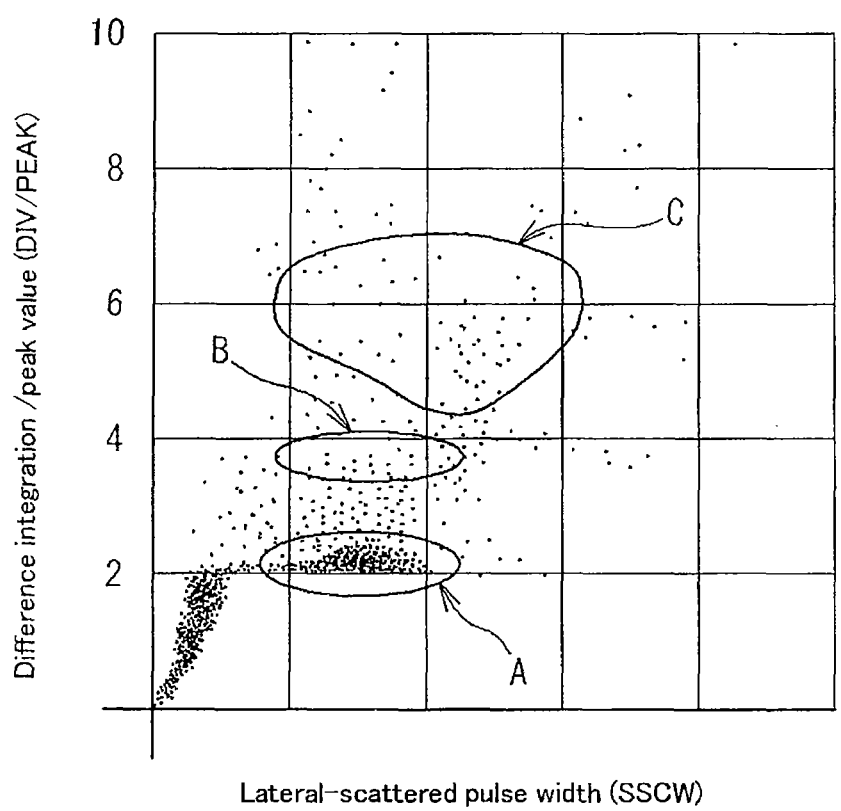
FIG. 6 is a scattergram in which the vertical axis shows values each of which is obtained by dividing a difference integration value of a fluorescence signal waveform of a measuring object cell by a peak value and the horizontal axis shows the pulse widths of side-scattered light signals.
Figure 7:
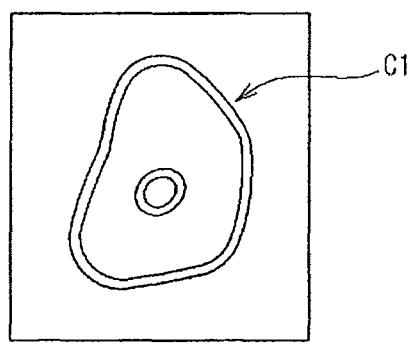
FIG. 7(a) shows a single cell (non-aggregating cell) C1.
FIG. 7(b) illustrates the signal waveform of a single cell.
Figure 7:
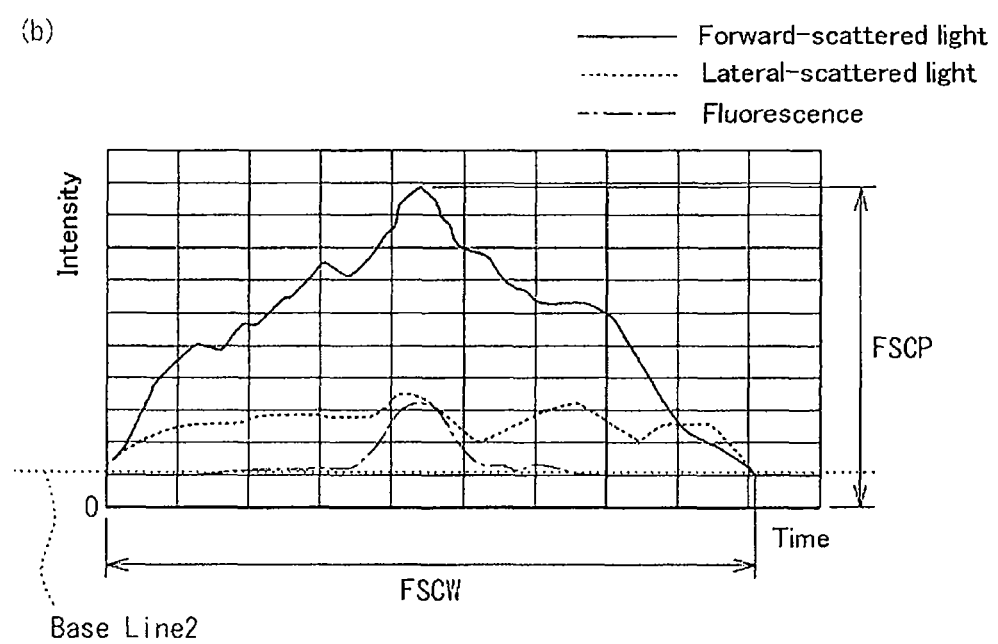

FIG. 6 is a (DIV/PEAK)-SSCW scattergram in which the vertical axis shows the value (DIV/PEAK) obtained by dividing the difference integration value (DIV) of the fluorescence signal waveform of the measuring object cell by the peak value (PEAK) and the horizontal axis shows the pulse width (SSCW) of the signal waveform of the lateral-scattered light. In FIG. 6, the cells distributed in the region shown by A have values on the vertical axis (difference integration value of fluorescence signal waveform/peak value (DIV/PEAK)) in a range from about 2 to 2.6. These cells are single cells (non-aggregating cells) C1 as shown in FIG. 7(*a*). FIG. 7(*b*) illustrates the signal waveform of the cell C1. As shown in FIG. 7(*b*), in the case of a single cell, the signal waveform peak is one, but the fluorescence signal waveform (chain line) shows a clearer peak when compared with the signal waveform of the forward-scattered light (solid line) and the signal waveform of the lateral-scattered light (broken line).

Figure 8:
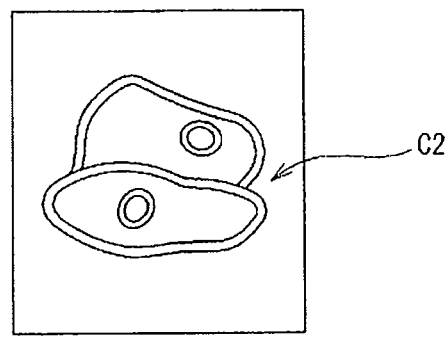
FIG. 8(a) shows aggregating cells C2 formed by aggregation of three cells.
FIG. 8(b) illustrates the signal waveform of an aggregating cell composed of two cells.
Figure 8:
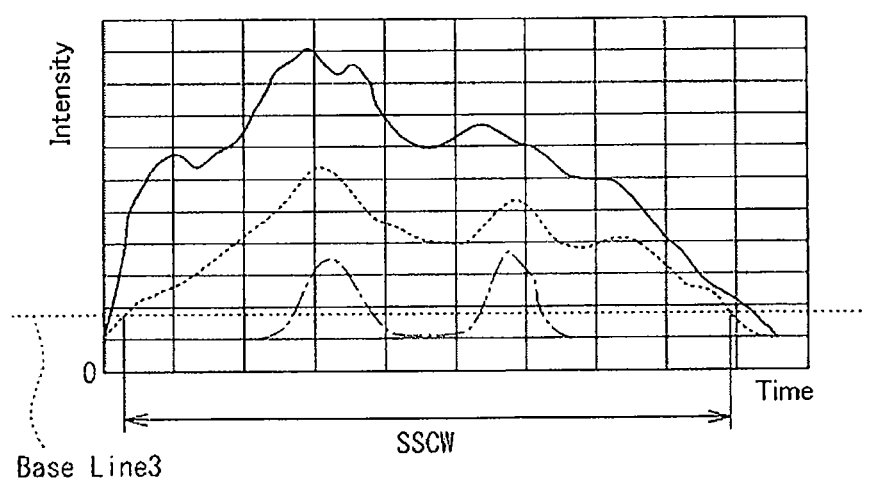

In FIG. 6, the cells distributed in the region shown by B have values on the vertical axis within a range from about 3.5 to 4.2. These samples are aggregating cells C2 formed by aggregation of two cells as shown in FIG. 8(*a*). In FIG. 6, the cells distributed in the region shown by C have values on the vertical axis within a range from about 4.5 to 7. These cells are aggregating cells C3 formed by aggregation of three cells as shown in FIG. 9(*a*). FIG. 8(*b*) illustrates the signal waveform of the cell C2. As shown in FIG. 8(*b*) and FIG. 9(*b*), the waveform of the fluorescence signal shows clearer peak and trough parts when compared with the signal waveform of the forward-scattered light and the signal waveform of the lateral-scattered light.

As described above, when compared with the signal waveform of the forward-scattered light and the signal waveform of the lateral-scattered light, the fluorescence signal waveform has clearer peak and trough parts. Thus, whether an aggregating cell or a non-aggregating cell can be determined accurately.

In the present embodiment, the beam spot has a diameter of 3 to 8 μm in the direction to which the measurement sample flows. Thus, the nucleus detection can have an improved S/N ratio. In the present embodiment, a nucleus is subjected to PI staining and a fluorescence signal from the nucleus is used. The PI staining causes a slightly-stained cell membrane in addition to the stained nucleus and also causes the rest of the dye used for the staining to be flowed in the flow cell, thus causing fluorescence from parts other than the nucleus. Therefore, the photomultiplier 59 (FIG. 4) as a fluorescence detector detects the fluorescence as noise from parts other than the nucleus. However, the lens system 52 of the optical detection section 3 reduces the diameter in the beam spot in the direction to which the measurement sample flows to 3 to 8 μm. Thus, a clearer distinction can be made between the fluorescence from the nucleus and the fluorescence from parts other than the nucleus. Specifically, by reducing the beam spot diameter to 3 to 8 μm in consideration of the nucleus size (5 to 7 μm), noise can be reduced to provide a sharp rise of the fluorescence signal pulse to thereby make the peak clear.

Figure 18:
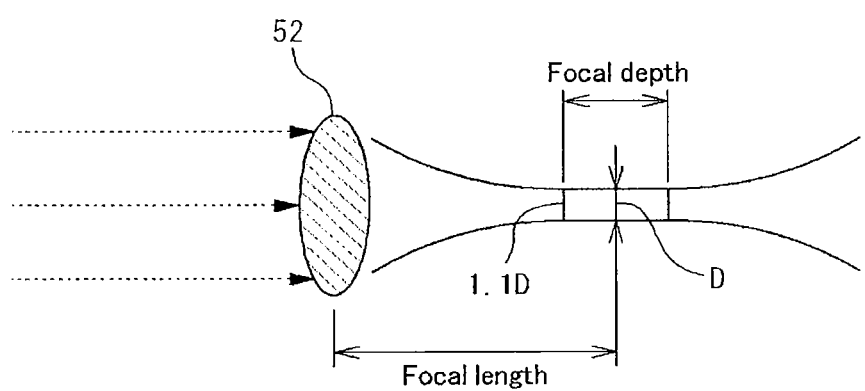
FIG. 18 illustrates the beam shape in the direction to which the measurement sample flows.

To make the diameter in the beam spot in the above flowing direction smaller than 3 μm, the lens system 52 must have a shorter focal length to cause a shallow region in which the laser beam has a stable intensity (focal depth). FIG. 18 illustrates the beam shape in the direction to which the measurement sample flows. As shown in FIG. 18, the focal depth shows a region covering up to a point at which the beam diameter becomes 1.1 times larger than the beam diameter D in the beam spot. As the beam diameter increases, the light intensity weakens. When the focal depth is shallow, laser beam cannot be stably emitted to the nucleus of the cell having a size of about 20 to 100 μm. On the other hand, when the diameter in the above flow direction is larger than 8 μm, the detection ratio of fluorescence as noise generated from parts other than the nucleus is increased. Thus, the rise of the fluorescence signal pulse is smooth to cause an obscure range of the pulse width of the fluorescence signal, thus deteriorating measurement accuracy. Furthermore, a plurality of cell nucleuses simultaneously pass through the beam spot with a higher frequency and the measurement accuracy deteriorates also from this point. Thus, it is preferable to select, in consideration of the above focal depth, the diameter in the beam spot in the direction to which the measurement sample flows. Specifically, the beam spot is preferably formed so that the laser beam narrowed in the direction to which the measurement sample flows has a focal depth of 20 to 110 μm. In order to stably emit laser beam to the nucleus, the beam spot diameter in the flow direction is preferably 3.5 to 7.5 μm and is more preferably 4 to 7 μm.

Since the beam spot diameter is within a range from 300 to 600 μm in the direction orthogonal to the direction to which the measurement sample flows, the entire epithelial cell of endocervix (about 60 μm) can pass a stable region of laser beam (a region in which the intensity is 0.95 or more when assuming that the laser beam forming the Gaussian distribution has a peak intensity of 1). As a result, stable scattered light can be obtained from the cell and the size of the cell can be measured accurately. Since the diameter in the direction orthogonal to the flow is 300 μm or more, the stable region of laser beam is increased and thus stable scattered light from the cell can be obtained. On the other hand, the diameter in the direction orthogonal to the flow of 600 μm or less increases the intensity of the laser beam close to the center and thus stable scattered light can be obtained. In order to obtain stable scattered light from the cell, the diameter in the direction orthogonal to the direction to which the measurement sample flows is preferably 350 to 550 μm.

Classification of Abnormal Cell

When cells changes to cancer and atypical cells, the cell division is activated to consequently cause the DNA amount to be higher than that of a normal cell. Thus, this DNA amount can be used as an indicator of cancer and atypical cells. As a value reflecting the DNA amount in the nucleus, an area of the pulse of a fluorescence signal from a measuring object cell irradiated with laser beam (fluorescence amount) (SFLI) can be used. As shown in FIG. 9(*b*), the area of the pulse of the fluorescence signal (fluorescence amount) (SFLI) shows the area surrounded by the base line (Base Line 1) and the fluorescence signal waveform. The signal processing circuit 4 acquires, based on the fluorescence signal output from the photomultiplier 59, the area of the pulse of the fluorescence signal (fluorescence amount) (SFLI) as a value reflecting the DNA amount of the nucleus of the measuring object cell. Then, the system control section 13 determines whether this fluorescence amount is equal to or higher than a predetermined threshold value or not. When this fluorescence amount is equal to or higher than the predetermined threshold value, the object cell is classified as a cancer and atypical cell having an abnormal DNA amount.

Figure 15:
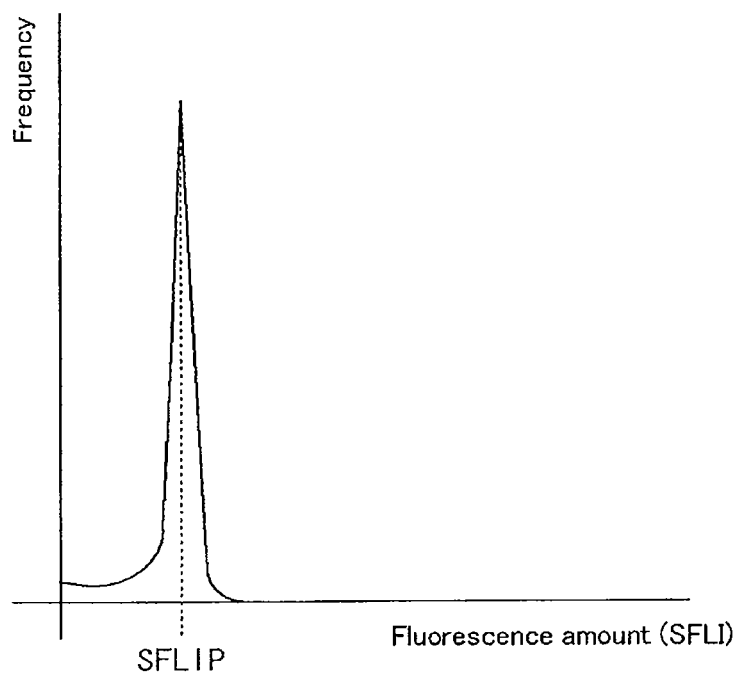
FIG. 15 is a histogram in which the horizontal axis shows the pulse areas of lateral fluorescence signals obtained from the measurement sample.

The most part of the sample used in the screening of a cervical cancer is composed of normal cells. Thus, when the histogram as shown in FIG. 15 is drawn in which the horizontal axis shows the area of the pulse of the fluorescence signal (fluorescence amount), a peak appears at a position corresponding to normal cells. The fluorescence amount at this peak position shows the DNA amount of normal cells. Thus, the system control section 13 classifies as abnormal cells those cells showing a 2.5 times or higher fluorescence amount than that of normal cells.

When two or more cells pass the beam spot of the laser beam while aggregating to one another, the fluorescence from a plurality of nucleuses is detected by the photomultiplier 59. Thus, a pulse having the entire large area is presumably output. However, as described above, according to the present embodiment, a value obtained by dividing the difference integration value of the fluorescence signal waveform by the peak value (DIV/PEAK) can be used to accurately exclude the data due to aggregating cells. This can consequently increase the classification accuracy of abnormal cells (cancer and atypical cells). Specifically, regarding those cells measured as having a high DNA amount because the cells are aggregating cells, these cells can be prevented from being mistakenly classified as abnormal cells.

A measurement sample may include, in addition to a measuring object cell, debris such as mucus, the remaining blood, and pieces of cells. When this debris is included in a high amount in the measurement sample, the fluorescence from the debris is detected as noise to thereby deteriorate the measurement accuracy. In this case, since the debris has a smaller size compared with the measuring object cell, the signal processing circuit 4 acquires, from the forward-scattered light signal outputted from the photodiode 55, the signal waveform pulse width of the forward-scattered light (FSCW) and the signal waveform peak value of the forward-scattered light (FSCP) as a plurality of parameters reflecting the sizes of particles including the measuring object cell. As shown in FIG. 7(*b*), the signal waveform peak value of the forward-scattered light (FSCP) shows the maximum intensity of the detected forward-scattered light (FSCP in FIG. 7(*b*)). The signal waveform pulse width of the forward-scattered light (FSCW) shows a signal waveform width of the forward-scattered light having a higher intensity than the base line (Base Line 2). The system control section 13 receives the forward-scattered light data including the signal waveform pulse width of the forward-scattered light (FSCW) and the signal waveform peak value of the forward-scattered light (FSCP) from the apparatus main body 12 via the external communication controller 25. Then, the system control section 13 prepares a scattergram using the signal waveform pulse width of the forward-scattered light (FSCW) and the signal waveform peak value of the forward-scattered light (FSCP) to thereby distinguish, based on the scattergram, between a measuring object cell and particles other than the measuring object cell (debris).

Figure 10:
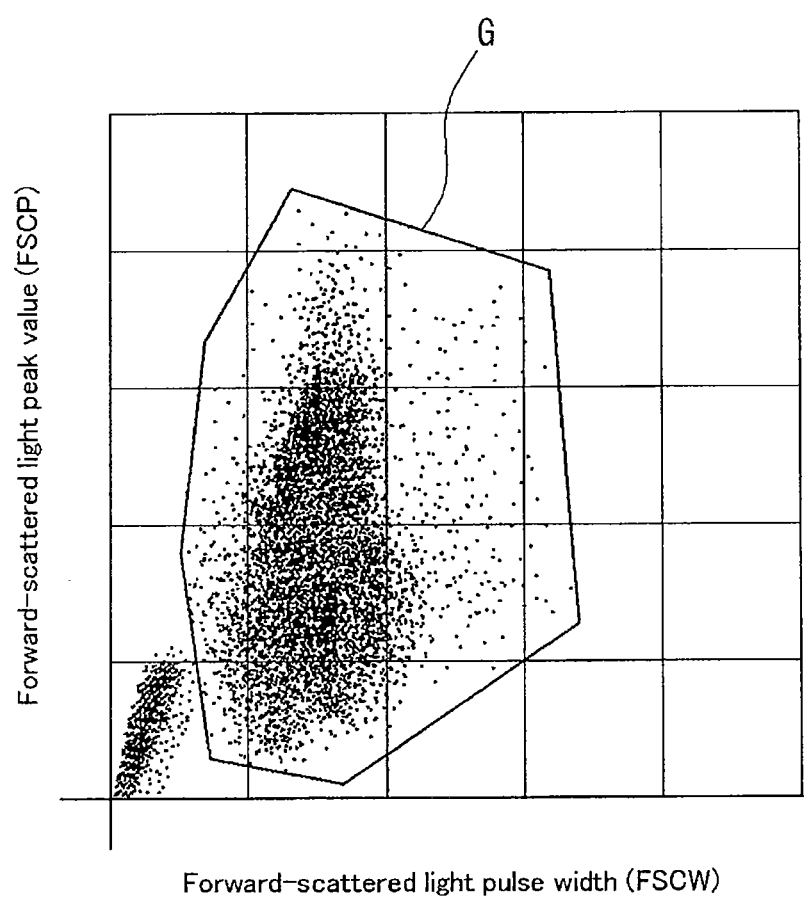
FIG. 10 is a scattergram in which the vertical axis shows the peak values of forward-scattered light signals obtained from the measurement sample and the horizontal axis shows the pulse widths of the forward-scattered light signals.

FIG. 10 is a FSCW-FSCP scattergram in which the horizontal axis shows the signal waveform pulse width of the forward-scattered light (FSCW) and the vertical axis shows the signal waveform peak value of the forward-scattered light (FSCP). Since a debris has a smaller size when compared with a measuring object cell, the signal waveform peak value of the forward-scattered light (FSCP) and the signal waveform pulse width of the forward-scattered light (FSCW), each of which reflects the size of particles, are smaller than the measuring object cell. In FIG. 10, one group distributed at the lower-left part shows debris. Thus, by assuming the cells in the region G as an analysis target in the subsequent process, the determination of an abnormal cell can be performed with a further higher accuracy.

Cell Analysis Method

Next, the following section will describe an embodiment of a cell analysis method using the cell analysis apparatus 10 (see FIG. 1).

First, a measurement sample to be flowed in a flow cell is manually prepared by a user. Specifically, a cell (epithelial cell) collected from the endocervix of a patient is subjected to known processes such as centrifugation (concentration), dilution (cleaning), agitation (tapping), or PI staining, thereby preparing a measurement sample.

Then, the user stores the prepared measurement sample in a test tube (not shown) and positions the test tube at the lower side of a pipette (not shown) of the apparatus main body.

Figure 11:
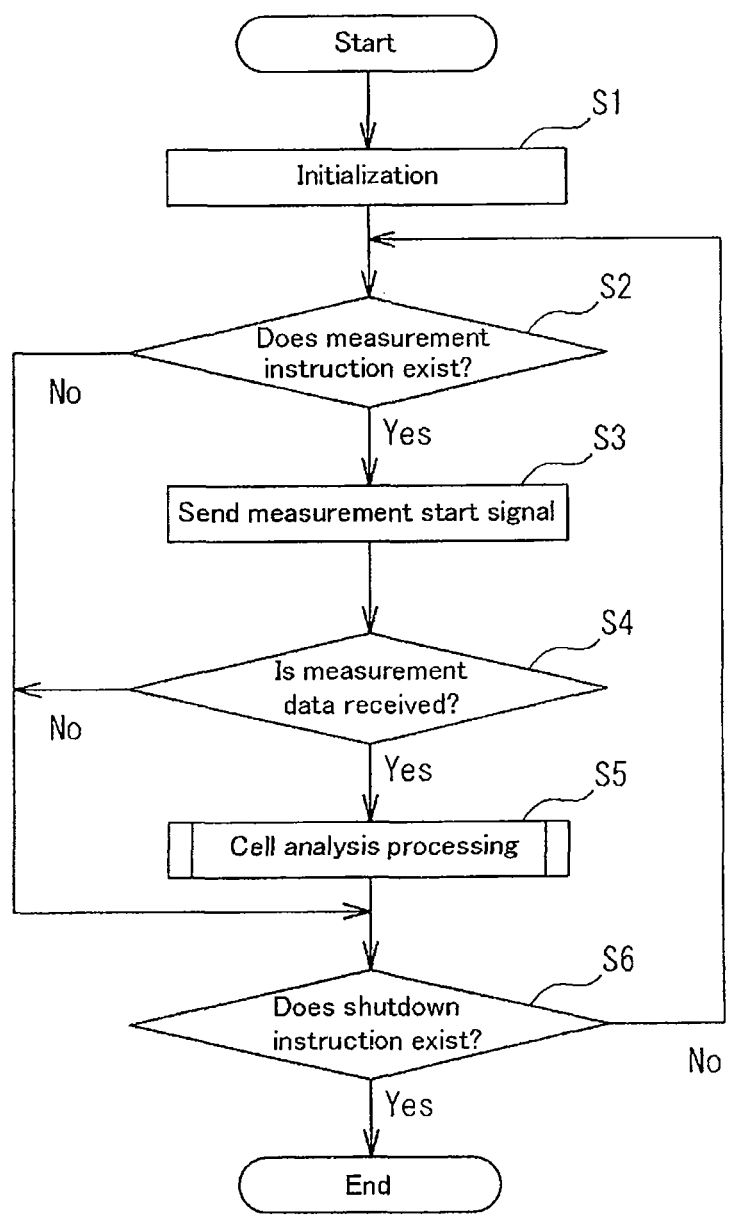
FIG. 11 is a flowchart illustrating the flow of the processing by the CPU of a system control section.
Figure 12:
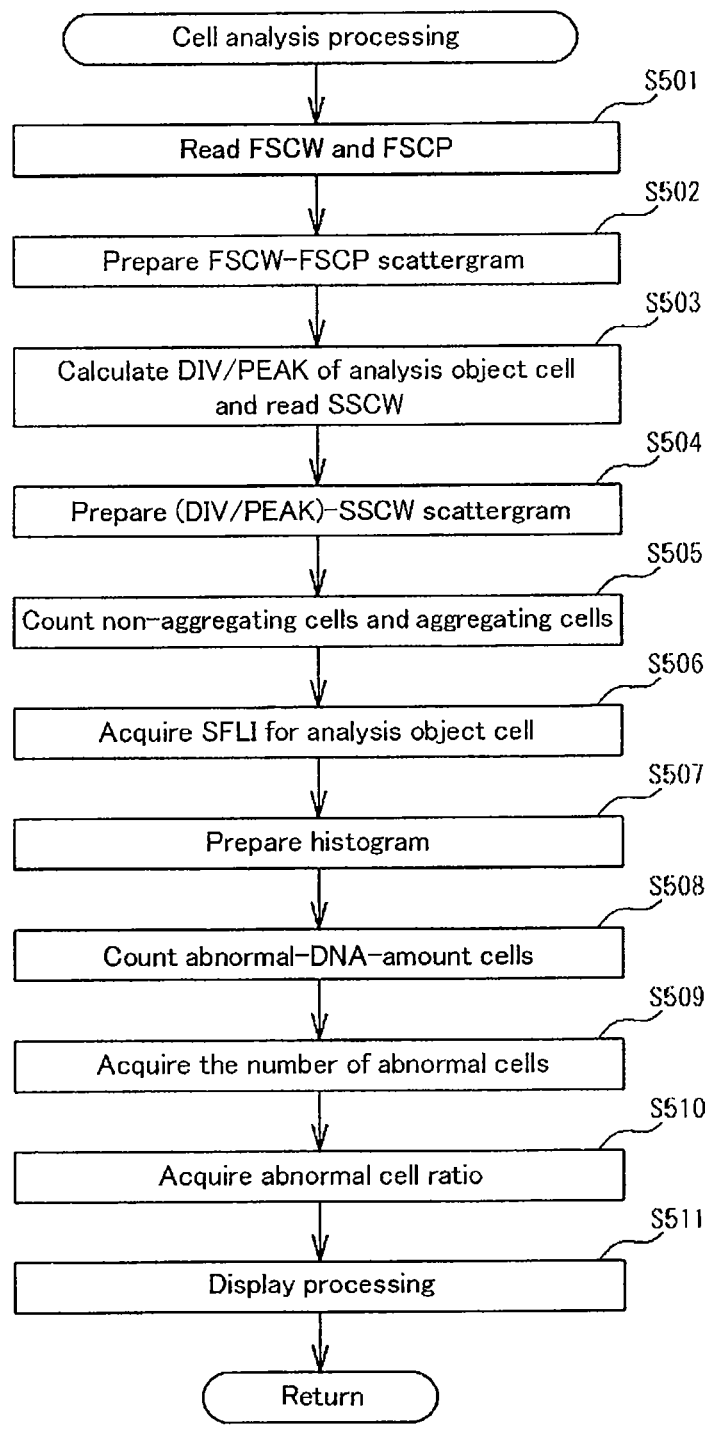
FIG. 12 is a flowchart illustrating the cell analysis processing by the CPU of the system control section.

Next, the following section will describe the flow of the processing by the system control section 13 with reference to FIG. 11 and FIG. 12.

First, when the power source of the system control section 13 is turned ON, the CPU 27a of the system control section 13 initializes a computer program stored in the system control section 13 (Step S1). Next, the CPU 27a determines whether a measurement instruction from the user is received or not (Step S2). When the measurement instruction is received, the CPU 27a sends a measurement start signal to the apparatus body 12 via an I/O interface 27f (Step S3). When the measurement instruction is not received, the CPU 27a proceeds to the processing of Step S6.

When the measurement start signal is sent to the apparatus main body 12, the measurement sample stored in the test tube is sucked by a pipette in the apparatus main body 12 and is supplied to the flow cell 51 shown in FIG. 4. Then, the measurement sample flowing in the flow cell 51 is irradiated with laser beam. Then, the forward-scattered light from the measurement sample is detected by the photodiode 55, the lateral-scattered light is detected by the photomultiplier 58, and the lateral fluorescence is detected by the photomultiplier 59.

Next, the forward-scattered light signal (FSC), the lateral-scattered light signal (SSC), and the fluorescence signal (SFL) outputted from the optical detection section 3 are sent to the signal processing circuit 4. Then, measurement data obtained by subjecting the signals to a predetermined processing by the signal processing circuit 4 is sent to the system control section 13 via the external communication controller 25.

On the other hand, the CPU 27a of the system control section 13 determines whether the measurement data (forward-scattered light data (FSC), the lateral-scattered light data (SSC), and the lateral fluorescence data (SFL)) is received from the apparatus main body 12 via the external communication controller 25 or not (Step S4). When the measurement data is received, the CPU 27a stores the measurement data in the hard disk 27d to subsequently execute a cell analysis processing (Step S5). When the measurement data is not received, the CPU 27a proceeds to the processing of Step S6.

After the cell analysis processing, the CPU 27a determines whether a shutdown instruction is received or not (Step S6). When the shutdown instruction is received, the CPU 27a completes the processing. When the shutdown instruction is not received, the CPU 27a returns to the processing of Step S2.

Next, the following section will describe the cell analysis processing of Step S5 with reference to FIG. 12.

First, the CPU 27a reads, from among the forward-scattered light data received from the apparatus main body 12, the signal waveform pulse width of the forward-scattered light (FSCW) and the signal waveform peak value of the forward-scattered light (FSCP) from the hard disk 27d and stores them into the RAM 27c (Step S501). Then, the CPU 27a prepares a FSCW-FSCP scattergram shown in FIG. 10 in which the horizontal axis shows the read pulse width (FSCW) and the vertical axis shows the peak value (FSCP) (Step S502). Then, the CPU 27a assumes the cells in the region G of this scattergram as an analysis target in the subsequent process. As a result, particles at the exterior of the region G are removed as the debris other than the measuring object cell.

Next, the CPU 27a reads, from among the lateral fluorescence data of the analysis object cell, the difference integration value of the fluorescence signal waveform (DIV) and the peak value of the fluorescence signal waveform (PEAK) from the hard disk 27d and stores them into the RAM 27c. Then, the CPU 27a acquires a value (DIV/PEAK) obtained by dividing the difference integration value of the fluorescence signal waveform (DIV) by the peak value of the fluorescence signal waveform (PEAK). The CPU 27a also reads, from among the lateral-scattered light data of the analysis target particles, the signal waveform pulse width of the lateral-scattered light (SSCW) from the hard disk 27d and stores them into the RAM 27c (Step S503). As shown in FIG. 8(b), the signal waveform pulse width of the lateral-scattered light (SSCW) shows the signal waveform width of the lateral-scattered light having a higher intensity than the base line (Base Line 3). The CPU 27a prepares a (DIV/PEAK)-SSCW scattergram shown in FIG. 6 in which the vertical axis shows the value (DIV/PEAK) obtained by dividing the difference integration value of the fluorescence signal waveform by the peak value and the horizontal axis shows the signal waveform pulse width of the lateral-scattered light (SSCW) (Step S504).

Then, the CPU 27a compares the value (DIV/PEAK) obtained by dividing the difference integration value of the fluorescence signal waveform (DIV) by the peak value of the fluorescence signal waveform (PEAK) with the threshold value of 2.6 to thereby determine whether the analysis target cell is an aggregating cell or a non-aggregating cell. When the following formula (1) is established, the cell is non-aggregating cell. When the formula (1) is not established, the cell is an aggregating cell.

$$DIV/PEAK \leq 2.6 \tag{1}$$

Then, the CPU 27a counts the respective number of non-aggregating cells and aggregating cells (Step S505).

Next, the CPU 27a reads, from among the lateral fluorescence data of the analysis object cell, the fluorescence amount (SFLI) that is a value reflecting the DNA amount of the nucleus of the measuring object cell and that shows the area of the pulse of the fluorescence signal from the hard disk 27d and stores them into the RAM 27c (Step S506). Then, the CPU 27a prepares a histogram shown in FIG. 15 in which the horizontal axis shows the area of the pulse of the fluorescence signal (fluorescence amount) (SFLI) (Step S507). In this histogram, a peak appears at a position corresponding to a normal cell.

Next, the CPU 27a determines whether or not the fluorescence amount (SFLI) of the analysis object cell is 2.5 times or more higher than the fluorescence amount (SFLIP) at the position in the histogram of FIG. 15 at which the peak appears, i.e., whether the following formula (2) is established or not.

$$SFLI \geq SFLIP \times 2.5 \tag{2}$$

Then, when the formula (2) is established, the CPU 27a classifies the cell as an abnormal-DNA-amount cell in which the DNA amount of the nucleus is abnormal. When the formula (2) is not established, the CPU 27a classifies the cell as a normal cell. Then, the CPU 27a counts those cells classified as abnormal-DNA-amount cells (Step S508). Next, the CPU 27a deducts the number of aggregating cells acquired in Step S505 from the number of abnormal-DNA-amount cells acquired in Step S508 to thereby acquire the number of abnormal cell (Step S509).

Next, the CPU 27a calculates a ratio between the number of non-aggregating cells acquired in Step S505 and the number of abnormal cells acquired in Step S509 to thereby acquire an abnormal cell ratio (Step S510). This abnormal cell ratio is a value functioning as an indicator for determining whether or not a sample analyzed by the cell analysis apparatus 10 includes therein a predetermined number or more of cancer and atypical cells. When the abnormal cell ratio is 1% or more for example, this means that the sample includes therein a predetermined number or more of cancer and atypical cells. Thus, the subject can know that he or she has a cancer with a high probability.

Then, the CPU 27a displays, on the display section 28 of the system control section 13 (see FIG. 1), the FSCW-FSCP scattergram prepared in Step S502, the (DIV/PEAK)-SSCW scattergram prepared in Step S504, and the histogram prepared in Step S507 as well as the abnormal cell ratio acquired in Step S510 via the image output interface 27g (FIG. 3) (Step S511). In the manner as described above, the cell analysis processing is executed by the CPU 27a.

The disclosed embodiment should be considered as illustrative in all points and should not be considered as limited. The scope of the present invention is defined not by the above description of the embodiment but by the claims, including the equivalents of the claims and all modifications within the scope.

For example, although the present embodiment has determined whether or not a sample collected from the subject includes therein a predetermined number or more of cancer and atypical cells of the endocervix, the cell analysis apparatus of the present invention is not limited to this. The present invention also can be used to determine whether or not a sample collected from the subject includes a predetermined number or more of cancer and atypical cells of buccal cells, other epithelial cells of bladder or throat for example, and an organ.

Although the present embodiment has displayed the abnormal cell ratio on the display section, the cell analysis apparatus of the present invention is not limited to this. The display section also can display not only the abnormal cell ratio but also a comment showing whether the subject has a cancer or not. This allows the subject to more easily know whether he or she has a cancer or not with a high probability.

Figure 16:
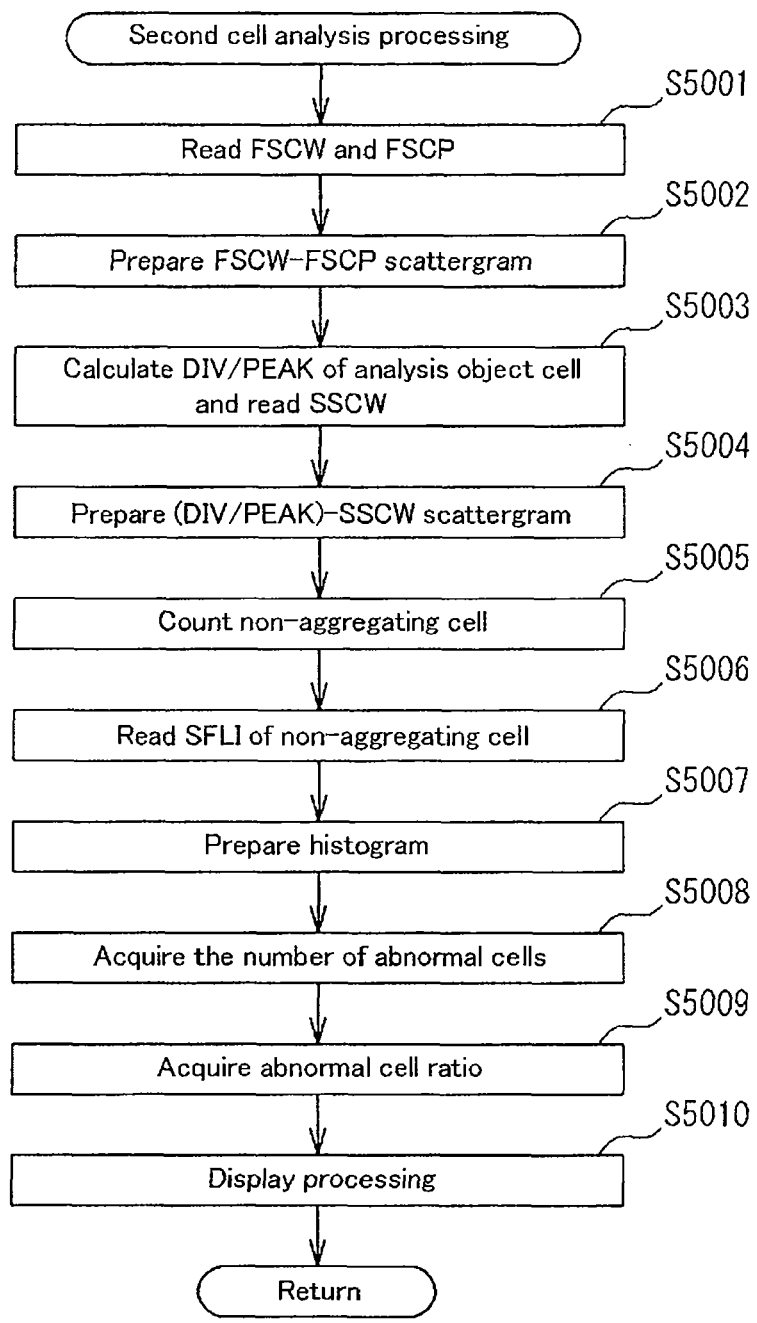
FIG. 16 is a flowchart illustrating the second cell analysis processing by the CPU of the system control section.

Although the present embodiment has acquired the number of aggregating cells to subsequently acquire the number of abnormal-DNA-amount cells and deducted the number of aggregating cells from the number of abnormal-DNA-amount cells to thereby acquire the number of abnormal cells (cancer and atypical cells), the embodiment of the present invention is not limited to this. FIG. 16 is a flowchart illustrating the second cell analysis processing by the CPU 27a of the system control section 13. The following section will describe the second cell analysis processing with reference to FIG. 16.

In the second cell analysis processing, the CPU 27a in Steps S5001 to S5004 executes the same processes as those of Steps S501 to S504 of the cell analysis processing shown in FIG. 12.

Next, the CPU 27a determines whether the formula (1) is established or not with regard to the cell as an analysis target in Step S5003. When the formula (1) is established, then the CPU 27a counts the cell as a non-aggregating cell (Step S5005).

Next, the CPU 27a reads the fluorescence amount (SFLI) of the non-aggregating cell for which the formula (1) is established from the hard disk 27d and stores them into the RAM 27c (Step S5006). Then, the CPU 27a prepares a histogram in which the horizontal axis shows the fluorescence amount (SFLI) (Step S5007).

Next, the CPU 27a classifies, as an abnormal cell (cancer and atypical cell), a cell showing a 2.5 times or more fluorescence amount than the fluorescence amount (SFLIP) at a position at which the peak appears in the histogram prepared in Step S5007 and counts the cell (Step S5008).

Next, the CPU 27a in Step S5009 executes the same processing as Step S510 of the cell analysis processing shown in FIG. 12 to acquire an abnormal cell ratio. Then, the CPU 27a displays, together with the FSCW-FSCP scattergram prepared in Step S5002, the (DIV/PEAK)-SSCW scattergram prepared in Step S5004, and the histogram prepared in Step S5007, the abnormal cell ratio acquired in Step S5009 on the display section 28 of the system control section 13 (see FIG. 1) (Step S5010) via the image output interface 27g (FIG. 3). In the manner as described above, the second cell analysis processing is executed by the CPU 27a.

Figure 17:
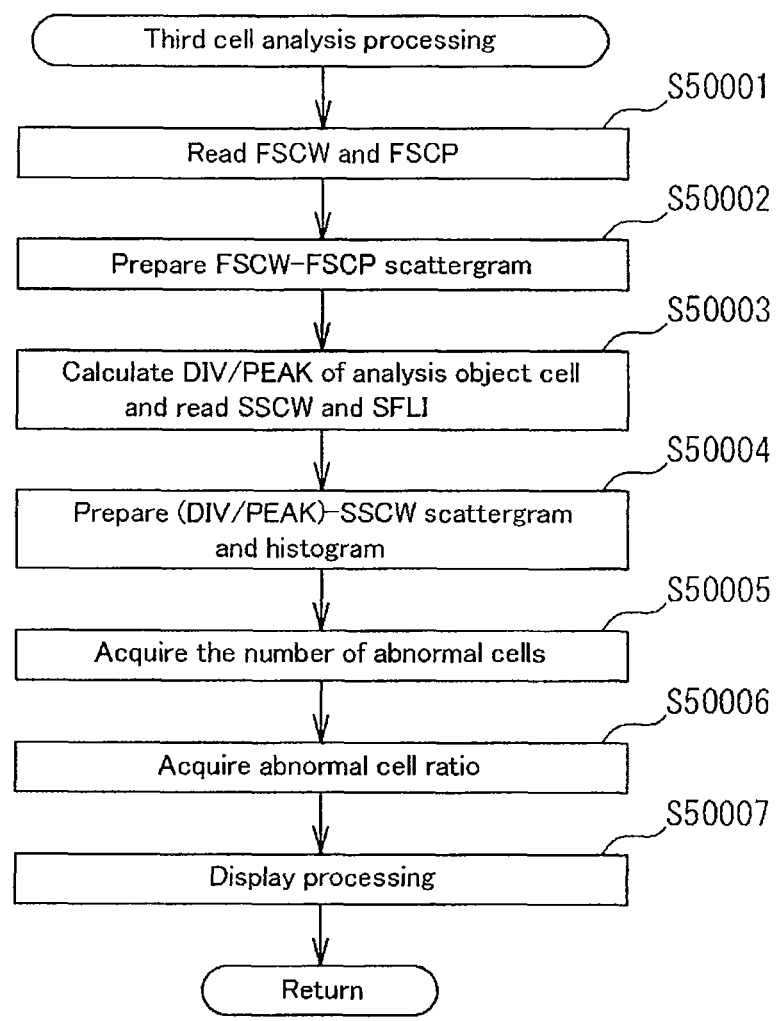
FIG. 17 is a flowchart illustrating the third cell analysis processing by the CPU of the system control section.

FIG. 17 is a flowchart illustrating the third cell analysis processing by the CPU 27a of the system control section 13. The following section will describe the third cell analysis processing with reference to FIG. 17.

In the third cell analysis processing, the CPU 27a in Steps S50001 and S50002 executes the same processes as Steps S501 and S502 of the cell analysis processing shown in FIG. 12.

Next, the CPU 27a reads, from among the lateral fluorescence data of the cell as an analysis target in Step S50002, the difference integration value of the fluorescence signal waveform (DIV), the peak value of the fluorescence signal waveform (PEAK), and the fluorescence amount (SFLI) as the area of the pulse of the fluorescence signal from the hard disk 27d and stores them into the RAM 27c. Then, the CPU 27a acquires the value (DIV/PEAK) obtained by dividing the difference integration value of the fluorescence signal waveform (DIV) by the peak value of the fluorescence signal waveform (PEAK). The CPU 27a also reads, from among the lateral-scattered light data of the analysis object cell, the signal waveform pulse width of the lateral-scattered light (SSCW) from the hard disk 27d and stores them into the RAM 27c (Step S50003). Then, the CPU 27a prepares a (DIV/PEAK)-SSCW scattergram in which the vertical axis shows the value (DIV/PEAK) obtained by dividing the difference integration value of the fluorescence signal waveform by the peak value and the horizontal axis shows the signal waveform pulse width of the lateral-scattered light (SSCW) and a histogram in which the horizontal axis shows the area of the pulse of the fluorescence signal (fluorescence amount) (SFLI) (Step S50004).

Next, the CPU 27a determines whether the formula (1) and the formula (2) are both established or not. When the formula (1) and the formula (2) are both established, the CPU 27a classifies the cell as an abnormal cell (cancer and atypical cell) and counts the cell (Step S50005). In the processing of this step, the CPU 27a counts the cell for which the formula (1) is established as a non-aggregating cell.

Next, the CPU 27a in Step S50006 executes the same processing as Step S510 of the cell analysis processing shown in FIG. 12 and acquires an abnormal cell ratio. Next, the CPU 27a displays, together with the FSCW-FSCP scattergram prepared in Step S50002 as well as the (DIV/PEAK)-SSCW scattergram and the histogram prepared in Step S50004, the abnormal cell ratio acquired in Step S50006 on the display section 28 of the system control section 13 (see FIG. 1) (Step S50007) via the image output interface 27g (FIG. 3). In the manner as described above, the third cell analysis processing is executed by the CPU 27a.

In the cell analysis apparatus 10, pigments for staining the nucleus of a measuring object cell is used to prepare a measurement sample and the fluorescence from the nucleus is detected by the detection section. As described above, the signal waveform of the forward-scattered light from the cell may have an unclear peak or trough part depending on the cell aggregating status or the cell flowing direction for example. However, the fluorescence signal waveform has clear peak and trough parts. Thus, the fluorescence from the nucleus can be used to accurately determine whether the cell is an aggregating cell or a non-aggregating cell.

What is claimed is:

1. A cell analysis apparatus for analyzing biological cells included in a measurement sample, comprising:
   a flow cell configured to flow the measurement sample which contains target objects each consisting of either a non-aggregating biological cell or an aggregation of biological cells, in which nuclei of the biological cells are dyed with a fluorescent dye,
   a laser configured to irradiate the target objects in the measurement sample flowing through the flow cell with a laser beam,
   a fluorescence detector configured to detect fluorescence light scattered from the nuclei in the target objects and outputs a fluorescent signal which carries size information of the respective nuclei in the target objects;
   a signal processing section configured to process the outputted fluorescence signal to acquire for a respective target object (i) a peak value reflecting a height of a fluorescence signal waveform, (ii) a difference integration value reflecting a length of a ridge line of the fluorescence signal waveform, and (iii) an area value of the fluorescent signal waveform reflecting a nuclear DNA amount in the respective target object;
   a processor in communication with the signal processing section and programmed to receive for the respective target object, from the signal processing section, the peak value, the difference integration value and the area value of the respective fluorescence signal waveform, wherein the processor is programmed to:
      for each target object, obtain a ratio of the difference integration value to the peak value;
      for each target object, compare the obtained ratio with a predetermined first threshold value and identify that a target object whose ratio is lower than the predetermined first threshold value is a non-aggregating biological cell; and
      for each identified non-aggregating biological cell, compare the area value with a predetermined second threshold value and determine that an identified non-aggregating biological cell whose area value is higher than the predetermined second threshold value has an abnormal amount of nuclear DNA.

2. The cell analysis apparatus according to claim 1, wherein
   the processor is programmed to:
   count the identified non-aggregating biological cells which are determined to have an abnormal amount of nuclear DNA; and
   output a relative population of the identified non-aggregating biological cells which are determined to have an abnormal amount of nuclear DNA with respect to a remaining population of the identified non-aggregating biological cells.

3. The cell analysis apparatus according to claim 1, further comprising a scattered light detector configured to detect a scattered light from the target objects in the measurement sample and output a scattered light signal which carries size information of the respective target objects,
   wherein the processor is programmed to apply the size information from the scattered light signal to distinguish the target objects from particles other than the biological cells.

4. The cell analysis apparatus according to claim 1, further comprising an optical system configured to focus the laser beam to form a beam spot on the measurement sample flowing through the flow cell, the beam spot having a diameter of 3 to 8 μm in a flow direction of the measurement sample and a diameter of 300 to 600 μm in a direction orthogonal to the flow direction of the measurement sample.

5. A cell analysis apparatus for analyzing biological cells included in a measurement sample, comprising:
   a flow cell configured to flow the measurement sample which contains target objects each consisting of either a non-aggregating biological cell or an aggregation of biological cells, in which nuclei of the biological cells are dyed with a fluorescent dye;
   a laser configured to irradiate the target objects in the measurement sample flowing through the flow cell with a laser beam;
   a fluorescence detector configured to detect fluorescence light scattered from the nuclei in the target objects and output a fluorescent signal which carries size information of the respective nuclei in the target objects;
   a signal processing section configured to process the outputted fluorescence signal to acquire for a respective target object (i) a peak value reflecting a height of a fluorescence signal waveform, (ii) a difference integration value reflecting a length of a ridge line of the fluorescence signal waveform, and (iii) an area value of the fluorescent signal waveform reflecting a nuclear DNA amount in the respective target object;

a processor in communication with the signal processing section and programmed to receive for the respective target object the peak value, the difference integration value and the area value of the respective fluorescent signal waveform from the signal processing section, wherein the processor is programmed to:

for each target object, obtain a ratio of the difference integration value to the peak value;

for each target object, apply a predetermined first threshold value to the obtained ratio to identify whether the respective target object is an aggregation of biological cells or a non-aggregating biological cell; and for each target object which is identified as a non-aggregating biological cell, applying a predetermined second threshold value to the area value to determine whether the non-aggregating biological cell is an abnormal cell or not.

6. The cell analysis apparatus of claim 1, further comprising a scattered light detector configured to detect at least one of forward scattered light and side scattered light from the target objects and output a scattered light signal which carries size information of the respective target objects, wherein the signal processing section applies the size information from the scattered light signal to the outputted fluorescence signal to identify a span of fluorescence waveform corresponding to each target object, and from each span of fluorescence waveform, acquires the peak value, the difference integration value and the area value.

7. The cell analysis apparatus of claim 1, wherein the biological cell is endocervix cell.

8. A cell analysis apparatus for analyzing biological cells included in a measurement sample, comprising:

a flow cell configured to flow the measurement sample which contains target objects each consisting of either a non-aggregating biological cell or an aggregation of biological cells, in which nuclei of the biological cells are dyed with a fluorescent dye, a laser configured to irradiate the target objects in the measurement sample flowing through the flow cell with a laser beam, a fluorescence detector configured to detect fluorescence light scattered from the nuclei in the target objects and output a fluorescent signal which carries size information of the respective nuclei in the target objects, a scattered light detector configured to detect at least one of forward scattered light and side scattered light from the target objects and output a scattered light signal which carries size information of the respective target objects;

a signal processing section configured to:

apply the size information from the scattered light signal to the outputted fluorescence signal to identify a span of fluorescence waveform corresponding to each target object; and from each span of fluorescence waveform, acquire for a respective target object (i) a peak value reflecting a height of the span of fluorescence waveform and (ii) a difference integration value reflecting a length of a ridge line of the span of fluorescence waveform;

a processor in communication with the signal processing section and programmed to receive for the respective target object, from the signal processing section, the difference integration value and the peak value of the respective spans of fluorescence waveform, wherein the processor is programmed to:

for each target object, obtain a ratio of the difference integration value to the peak value; and for each target object, apply a predetermined first threshold value to the obtained ratio to determine whether the corresponding target object is an aggregation of a plurality of biological cells or a non-aggregating biological cell.

* * * * *